(12) United States Patent
Davis et al.

(10) Patent No.: US 12,194,205 B2
(45) Date of Patent: Jan. 14, 2025

(54) MULTI-LAYER AIR FILTRATION MEDIA WITH INTEGRATED DISINFECTION CAPABILITY

(71) Applicant: Research Triangle Institute, Research Triangle Park, NC (US)

(72) Inventors: James Lynn Davis, Holly Springs, NC (US); Howard Jerome Walls, Apex, NC (US); Karmann C. Mills, Apex, NC (US); David Edward Dausch, Raleigh, NC (US)

(73) Assignee: RESEARCH TRIANGLE INSTITUTE, Research Triangle Park, NC (US)

( * ) Notice: Subject to any disclaimer, the term of this patent is extended or adjusted under 35 U.S.C. 154(b) by 888 days.

(21) Appl. No.: 17/245,529

(22) Filed: Apr. 30, 2021

(65) Prior Publication Data

US 2021/0338879 A1 Nov. 4, 2021

Related U.S. Application Data

(60) Provisional application No. 63/017,950, filed on Apr. 30, 2020.

(51) Int. Cl.
*A61L 9/20* (2006.01)
*A62B 17/00* (2006.01)
*A62B 23/02* (2006.01)

(52) U.S. Cl.
CPC .............. *A61L 9/20* (2013.01); *A62B 17/006* (2013.01); *A62B 23/02* (2013.01); *A61L 2209/111* (2013.01); *A61L 2209/12* (2013.01); *A61L 2209/14* (2013.01); *A61L 2209/16* (2013.01)

(58) Field of Classification Search
CPC ....... A41D 31/305; A61L 9/20; A62B 17/006; A62B 23/00; A62B 23/02; F24F 1/02; F24F 13/28
See application file for complete search history.

(56) References Cited

U.S. PATENT DOCUMENTS

| | | | |
|---|---|---|---|
| 5,892,621 | A | 4/1999 | McGregor et al. |
| 6,872,241 | B2 | 3/2005 | Soane et al. |
| 7,585,451 | B2 | 9/2009 | Bryner et al. |
| 7,789,930 | B2 | 9/2010 | Ensor et al. |
| 7,999,455 | B2 | 8/2011 | Davis et al. |
| 8,652,229 | B2 | 2/2014 | Ensor et al. |
| 8,714,776 | B2 | 5/2014 | Han et al. |
| 8,864,341 | B2 | 10/2014 | Davis et al. |

(Continued)

FOREIGN PATENT DOCUMENTS

CN 103398423 A * 11/2013

OTHER PUBLICATIONS

Sliney, Part 2-Spread of SARS-COV-2 and a Potential Role of UV-C for Air and Surface Disinfection, the 2019 time frame.

(Continued)

*Primary Examiner* — Sharon Pregler
(74) *Attorney, Agent, or Firm* — IP & T GROUP LLP

(57) ABSTRACT

An air filtration media with integrated disinfection capability. The media has a collection filter for capture of pathogens, and an ultraviolet (UV) radiation source integrated into the collection filter such that the pathogens collected by the collection filter are exposed to UV radiation from the UV radiation source.

25 Claims, 11 Drawing Sheets

(56) References Cited

U.S. PATENT DOCUMENTS

| | | |
|---|---|---|
| 8,884,507 B2 | 11/2014 | Davis et al. |
| 9,228,716 B2 | 1/2016 | Davis et al. |
| 9,981,056 B2 | 5/2018 | Al-Zeer et al. |
| 9,988,664 B2 | 6/2018 | Ensor et al. |
| 10,099,165 B2 | 10/2018 | Walls et al. |
| 10,188,973 B2 | 1/2019 | Clayton et al. |
| 10,208,331 B2 | 2/2019 | Ensor et al. |
| 10,328,372 B2 | 6/2019 | Mazumder et al. |
| 10,335,618 B2 | 7/2019 | Zhou et al. |
| 10,363,327 B2 | 7/2019 | Liao et al. |
| 10,378,042 B2 | 8/2019 | Ensor et al. |
| 2003/0086848 A1 | 5/2003 | Saccomanno |
| 2009/0160099 A1 | 6/2009 | Huang |
| 2009/0232902 A1 | 9/2009 | Liu et al. |
| 2010/0034914 A1 | 2/2010 | Petras et al. |
| 2010/0247908 A1 | 9/2010 | Velev et al. |
| 2011/0052462 A1 | 3/2011 | Schmidt et al. |
| 2017/0321877 A1 | 11/2017 | Polidoro |

OTHER PUBLICATIONS

International IUVA Ultraviolet Association, IUVA Fact Sheet on COVID-19, the 2020 time frame.

\* cited by examiner

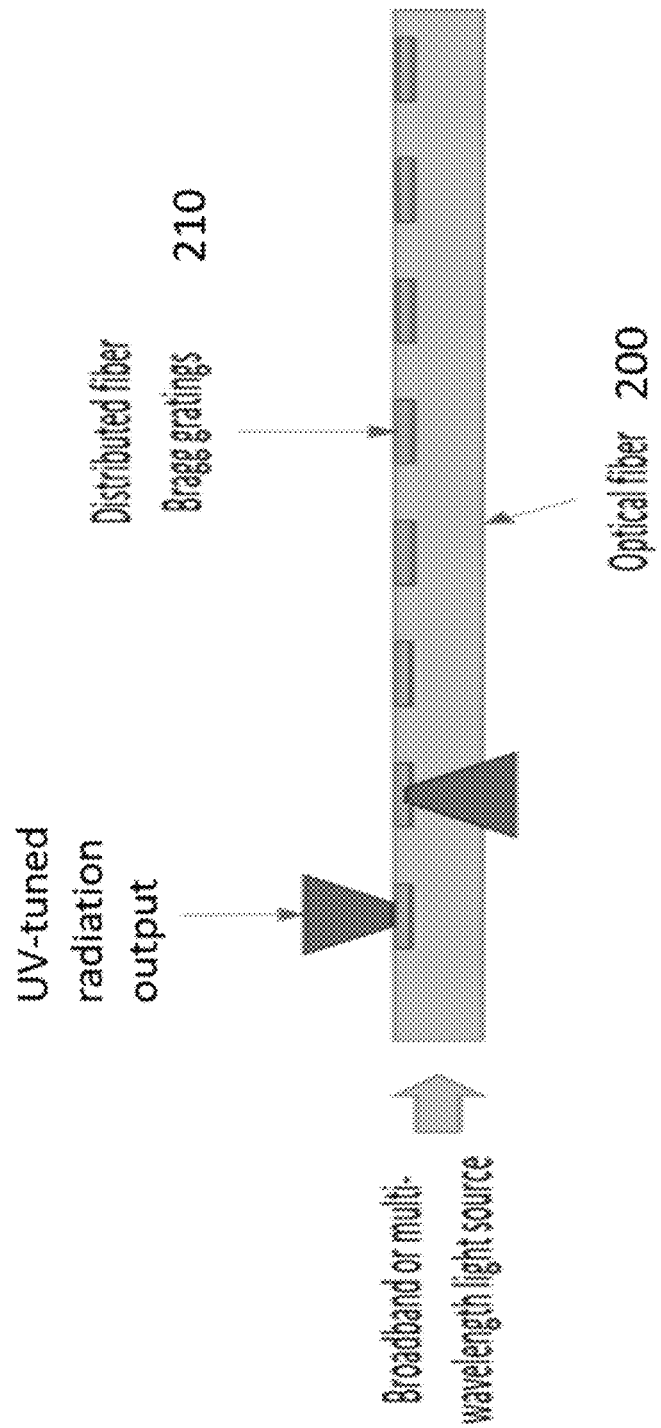

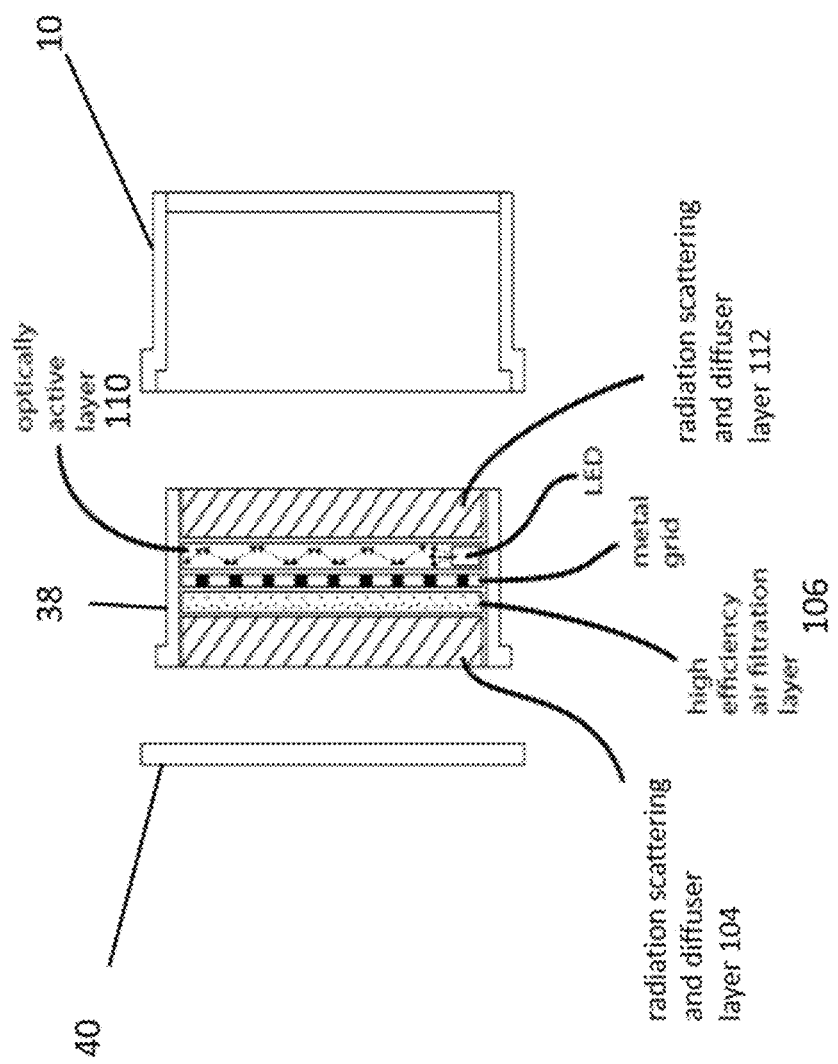

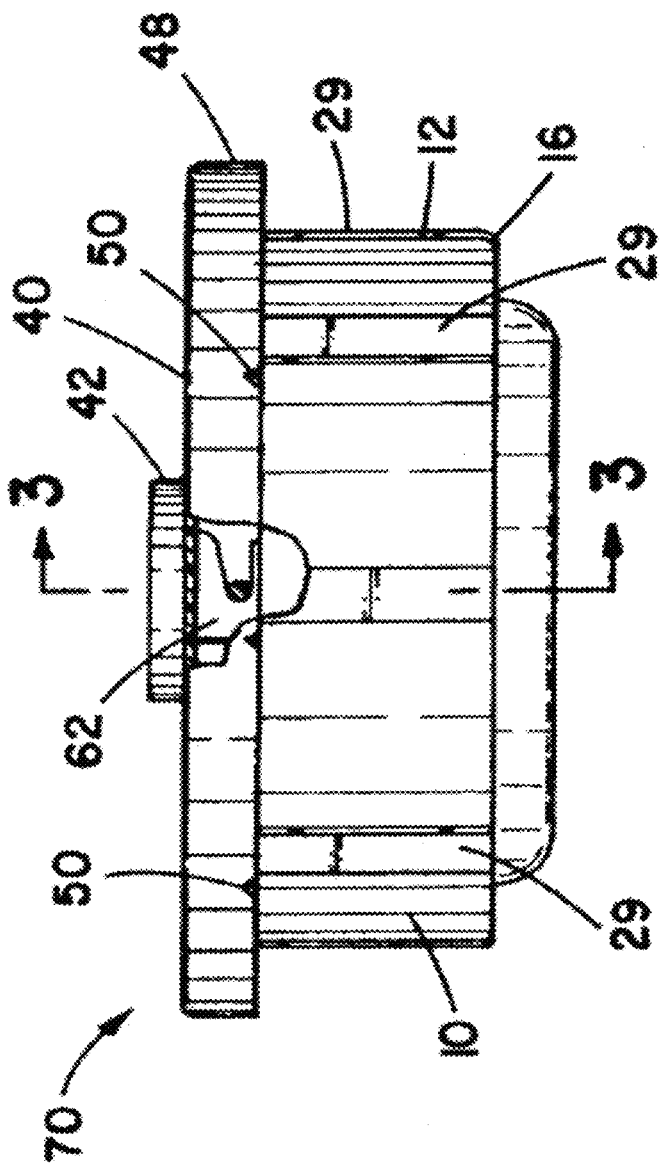

MULTI-LAYER AIR FILTRATION MEDIA WITH INTEGRATED DISINFECTION CAPABILITY

CROSS REFERENCE TO RELATED APPLICATIONS

This is application is related to and claims priority to U.S. Ser. No. 63/017,950, entitled "MULTI-LAYER AIR FILTRATION MEDIA WITH INTEGRATED DISINFECTION CAPABILITY," the entire contents of which are incorporated herein by reference. This application is also related to the following patents and patent applications, the entire contents of each of which are incorporated herein by reference. U.S. Pat. Nos. 7,789,930; 8,652,229; 9,988,664; 10,099,165; 10,188,973; 10,208,331; 10,378,042; 7,999,455; 8,714,776; 8,864,341; 8,884,507; 9,228,716.

BACKGROUND OF THE INVENTION

Field of Invention

The invention relates to an air filtration media for use in medical or other areas where the air is contaminated or potentially contaminated with pathogens.

Discussion of the Background

Air filtration media are used to capture airborne or aerosol particles and prevent them from being inhaled in the lungs, absorbed through the skin, or transferred through the mouth, eyes, and nose. Air filtration media can be comprised of non-woven materials formed by random arrangement of fibers (e.g., nanofibers, microfibers) or porous media (e.g., Gore-tex) that allow air to pass through the structure but also permit the capture of particles through a variety of mechanisms (e.g., interception, impaction, diffusion, electrostatic attraction). The efficiency of particle collection for the filtration media is a function of media composition (i.e., pore size and media thickness). Certain constructs of nanofiber filters have been shown to have high collection efficiency with minimal pressure drop. These constructions as described in part by the following U.S. Pat. Nos. 7,789,930; 8,652,229; 9,988,664; 10,099,165; 10,188,973; 10,208,331; 10,378,042.

In addition, nanofiber and nanoporous media have been shown to provide the ability to diffusely scatter electromagnetic radiation, and the ability of such media to scatter electromagnetic radiation is dependent on the ratio of the wavelength of electromagnetic radiation and the pore size of the media. This technology is described in multiple patents including the following U.S. Pat. Nos. 7,999,455; 8,714,776; 8,864,341; 8,884,507; 9,228,716.

As in air filter, the pore size in nanofiber materials used to scatter electromagnetic radiation is defined as the three-dimensional interstitial spacing between nanofibers comprising the mat. In nanoporous materials (e.g., DRP® diffuse reflector from W.L. Gore), scattering of electromagnetic radiation occurs at small porous sites in the expanded polytetrafluoro-ethylene (e-PTFE) material. This technology is described in U.S. Pat. No. 5,892,621 (the entire contents of each of which are incorporated herein by reference). Both nanofiber and e-PTFE materials can provide diffuse scattering of electromagnetic radiation solely due to the index of refraction mismatch that occurs at the interface of solid materials (e.g., fiber or PTFE, material) and pores.

The following patents and patent applications (the entire contents of which are incorporated herein by reference) are characteristic of the background:

1. U.S. Pat. No. 6,872,241 entitled: Anti-pathogenic air filtration media and air handling devices having protective capabilities against infectious airborne microorganisms;
2. U.S. Pat. No. 9,981,056 entitled: Air treatment system;
3. U.S. Pat. No. 10,328,372 entitled: Anti-microbial air filter;
4. U.S. Pat. No. 10,335,618 entitled: Breathing apparatus with ultraviolet light emitting diode;
5. U.S. Pat. No. 10,363,327 entitled: Luminaire with white light LEDs and UV LEDs for lighting and disinfection;
6. U.S. Pat. Appl. Publ. No. 20030086848 entitled: Ultraviolet disinfecting apparatus;
7. U.S. Pat. Appl. Publ. No. 20110052462 entitled: Filters for removal of volatile siloxanes and lifetime extension of photocatalytic devices;
8. U.S. Pat. Appl. Publ. No. 20170321877 entitled: Wall-mounted hospital bed, health care facility, or other wall (or surface) type light with ultraviolet-C germicidal (or other) air decontamination system.

SUMMARY OF THE INVENTION

In one embodiment, there is provided an air filtration media with integrated disinfection capability. The media has a collection filter for capture of pathogens, and an ultraviolet (UV) radiation source integrated into the collection filter such that the pathogens collected by the collection filter are exposed to UV radiation from the UV radiation source.

In one embodiment, there is provided at least one of a respirator, a laminated face mask, a garment, an air flow filter, and a HVAC unit comprising the air filtration media with integrated disinfection capability discussed above.

In one embodiment, there is provided a method for sterilizing pathogens using the air filtration media with integrated disinfection capability discussed above.

It is to be understood that both the foregoing general description of the invention and the following detailed description are exemplary, but are not restrictive of the invention.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 5 is a schematic a fiber optic with Bragg diffraction gratings etched into the surface to permit electromagnetic radiation "leakage" at select points;

FIG. 6A is a side view of the respirator cartridge shown in FIG. 1 including a multi-layer air filtration media with an integrated disinfection function;

FIG. 7 is a side view of the respirator cartridge shown in FIG. 1 when assembled;

DETAILED DESCRIPTION OF THE INVENTION

The present invention is directed to a multi-layer air filtration media 100 with an integrated disinfection function having the capability to destroy any viruses, bacteria, or biological agent that has been retained by the media. In one embodiment, a high efficiency media effectively and efficiently captures most particles, and the integrated disinfection function provides a way to neutralize the biological material so that the air filtration media can be safely reused without further threat or risk of re-exposure. In one embodiment of the invention (as noted above), air filtration media with integrated disinfection capability is provided. The air filtration media with integrated disinfection capability comprises a collection filter for capture of pathogens, and an ultraviolet (UV) radiation source integrated into the collection filter such that the pathogens collected by the collection filter are exposed to UV radiation from the UV radiation source. As used herein and unless otherwise defined in the claims, pathogens are any kind of bacterium, virus, fungi, or other microorganism or toxin that can cause disease or otherwise sicken a patient. As used herein and unless otherwise defined in the claims, integrated means made with, composed with, attached to, assembled together, combined together, made into a structure, and/or working together to form a complete unit with the recited "integrated" elements. As used herein, disinfection means destruction. sterilization, inactivation, making void of and/or nullifying any kind of bacterium, virus, fungi or other microorganism or toxin that would normally be expected to cause disease or otherwise sicken a patient. As used herein, disinfection includes complete or partial reduction in infectious activity of any kind of bacterium, virus, fungi, or other microorganism or toxin that normally would be expected to cause disease or otherwise sicken a patent. Disinfection is typically expressed in logarithm decrease in activity with 2 to 4 log reduction being considered complete disinfection. As such disinfection used herein means any reduction in activity including as low as 0.5 to 1 log and as much as 4 or greater log reduction. Note that disinfection is not cleaning or removal of accumulated material, just the removal of activity. As used here disinfection may include degradation or partial delegation of biological material present.

Figure 1A:
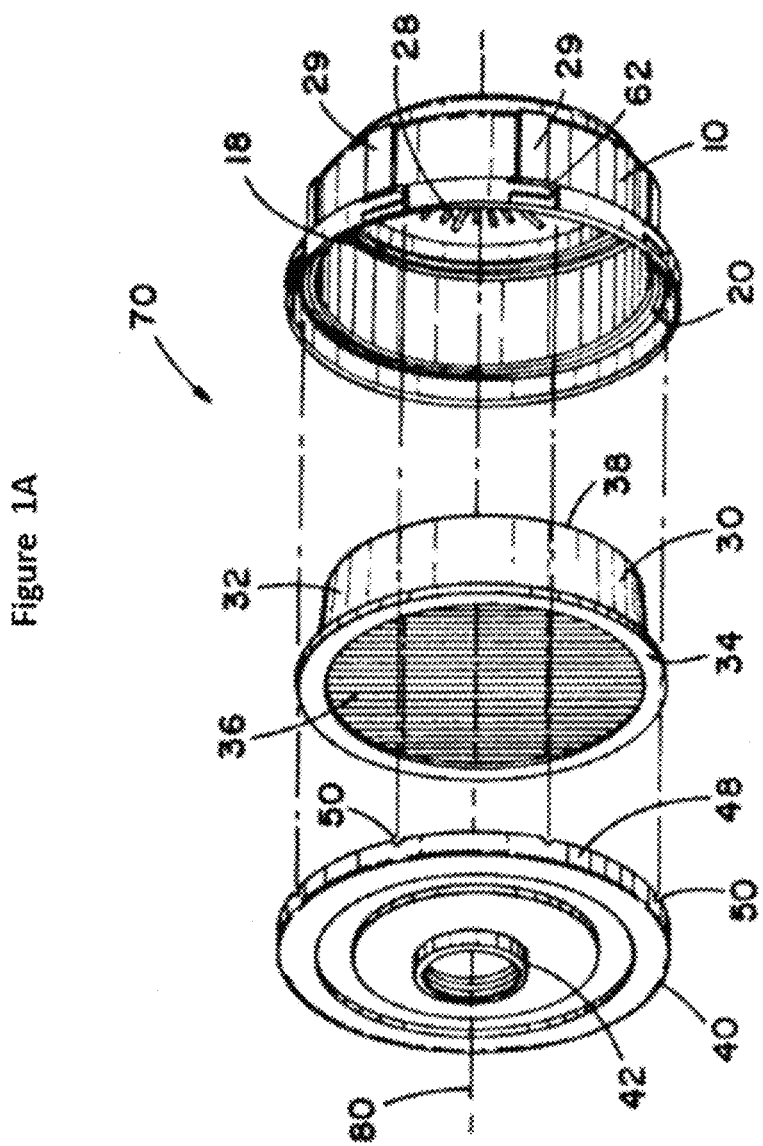
FIG. 1A is an exploded perspective view of a respirator cartridge including a housing, a filter, and a cover according to the present invention.

FIG. 1A is a schematic illustrating a conventional respirator cartridge 70 consisting of a housing 10, a filter 30, and a cover 40 which are centered on, and aligned along a central axis 80.

Housing 10 has a substantially cylindrical shape with an annular peripheral wall 12, an upper edge 14, a lower edge 16, a base with a peripheral filter support surface 18, a peripheral sealing surface 20 extending outwardly from upper edge 14, and a second annular peripheral wall 22 extending upwardly from an outer edge of sealing surface 20.

A respirator latch 42, filter element 36, and a vented opening 28 on the opposite end of cartridge 70 form an air passage through cartridge 70. Although, functionally, respirator latch 42 could be located on either end of cartridge, it is located on cover 40 and vented opening 28 is located on the bottom of housing 10.

Replaceable filter 30 has a filter element 36 molded into an annular peripheral frame 32 with a sealing lip 34 extending outwardly from one end. When filter 30 is disposed in housing 10, sealing lip 34 rests on sealing surface 20 of housing and bottom of filter frame 38 rests on filter support surface 18. The distance between bottom of filter frame 38 and bottom of sealing lip 34 is the same as the distance between filter support surface 18 and sealing surface 20 of housing. Filter frame 32 diameter at bottom of sealing lip 34 is the same as the inner diameter of annular peripheral wall 12, but tapers to a smaller diameter at bottom of filter frame 38 to facilitate insertion and removal of filter 30.

Figure 1B:
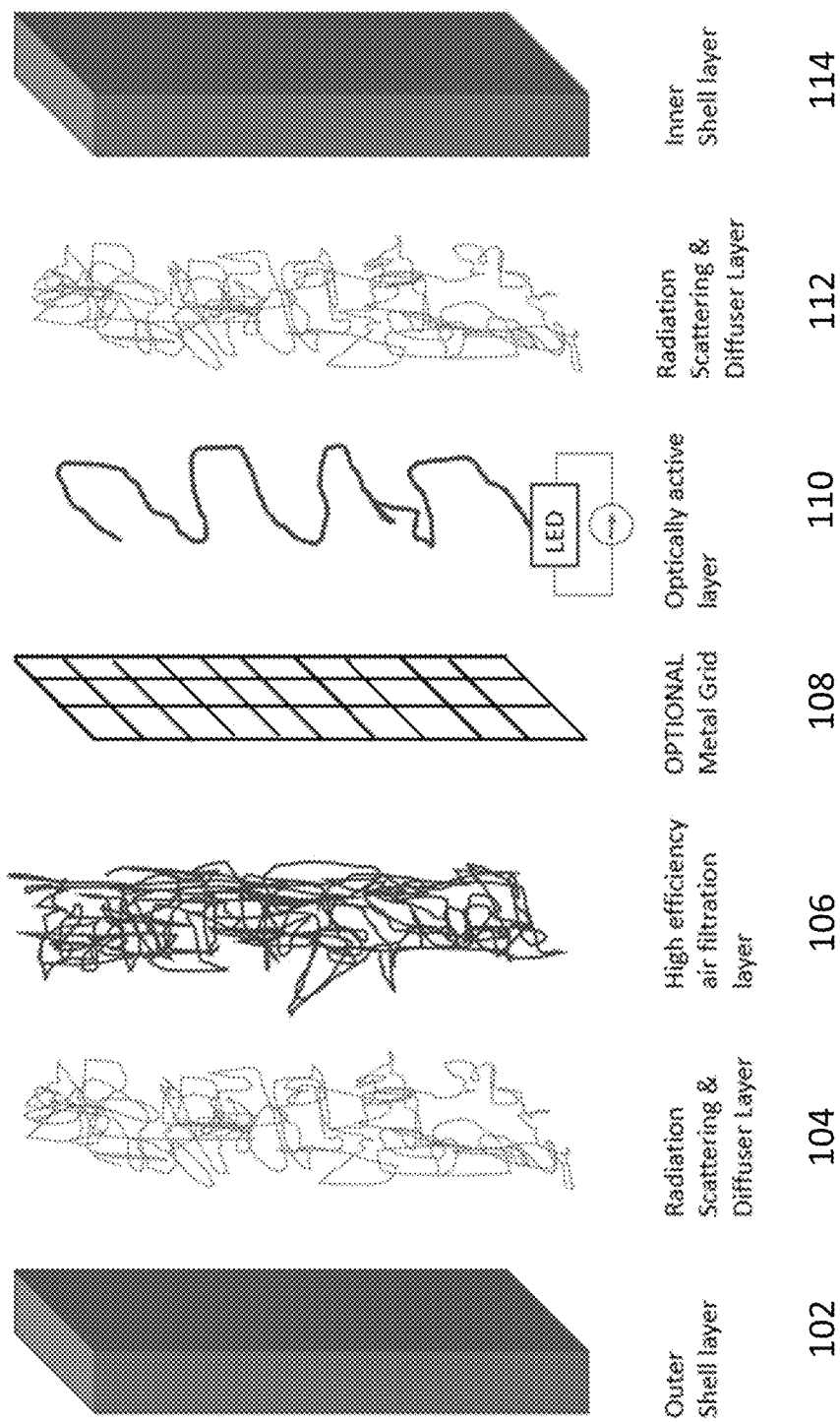
FIG. 1B is a schematic illustration of the components of air filtration medium with integrated disinfection capability.

Meanwhile, FIG. 1B shows the inventive air filtration media 100 with integrated disinfection capability in which viruses and pathogens are trapped on a high efficiency air filtration layer (preferably, but not necessarily the high FoM patterned nanofiber filters described below) and where the viruses and pathogens are sterilized by UV radiation generated from a UV radiation emitting LED contained therein. The sterilizing filtration medium in this embodiment comprises first shell layer 102, a first electromagnetic radiation scattering and diffuser layer 104, a particle capture layer 106 preferably but not necessarily, formed of a high efficiency air filtration media, an optional wire mesh layer 108, an optically active layer 110, a second electromagnetic radiation scattering and diffuser layer 112, and a second shell layers 114. All or some of the elements 102-114 may replace filter 30 in the conventional respirator shown in FIG. 1A. More detail will follow.

The composite structure shown in FIG. 1B functions by capturing viral, bacterial, or other biological pathogens on the high efficiency filtration media. The pore diameter of the filter media is chosen to have high collection efficiency with minimal pressure drop. The captured virus, bacterial, or other biological pathogen is then subjected to electromagnetic radiation to kill or deactivate the biological material. The effectiveness of the disinfection is proportional to the wavelength of electromagnetic radiation that is used and the total photon dose (i.e., photon radiant flux multiplied by time). The construction of the electromagnetic radiation diffusion media is chosen to scatter the electromagnetic radiation uniformly to ensure high radiant flux densities, and the pore diameter and material thickness is chosen so that the total pressure drop across the media is within acceptable limits for the application. This material is also chosen to contain most of the electromagnetic radiation within the structure. The inner and outer shells are structured to provide physical protection to the inner layers (i.e., electromagnetic radiation diffuser, high efficiency air filtration media, and fiber optic). The shell layers may also contain pigments and additives to promote the absorption of any electromagnetic radiation that leaks pass the scattering and diffuser layers.

The composite structure shown in FIG. 1B has multiple uses including: a) utilization as part of a face mask such as an N95 mask worn by medical professionals or others exposed to potential biological hazards, b) utilization for cartridges in respirators such as the one shown in FIG. 1A and those worn by medical professionals or first responders exposed to potentially severe levels of biological hazards, c) utilization in flat or pleated filtration media such as would be found in the heating, ventilation, and air condition (HVAC) systems of most residences, offices, schools, and public buildings, and d) utilization in hospital gowns and other forms of clothing worn as personal protection equipment.

Returning to FIG. 1B, the inner and outer shell layers (first shell layer 102 and second shell layer 114) provide protection during handling. These shell layers 102, 114 may be a non-woven or woven material and of sufficient porosity to provide easy passage of air with minimal resistance. The inner and outer shells encase the layers described below and can contain pigments to absorb any excess electromagnetic radiation produced within the mask. In addition, these layers can be coated to prevent moisture absorption.

The first and second electromagnetic radiation scattering and diffuser layers 104, 112 shown in FIG. 1B are formed of a material known to diffusely scatter electromagnetic radiation (such as a nanofiber radiation diffuser or e-PTFE radiation diffuser) as described above. These layers 104, 112 can be made of a material that is non-absorbing to the electromagnetic radiation produced within the assembly. Examples of such materials include fibrous and/or nanoporous materials made from cyclic olefin copolymers (COC) such as TOPAS® (see topas.com/uv-transparency), PTFE, e-PTFE, polyvinylidene fluoride, fluorinated ethylene propylene, polyether ether ketone (PEEK), quartz, and other mineral materials. All of the web articles and web linked materials noted herein are incorporated herein in their entirety by reference.

The particle capture layer 106 shown in FIG. 1B is preferably formed of a high efficiency air filtration media (such as a nanofiber filter like those described above or an air filtration media from W.L. Gore or Welcron H-11 or H-12 nonwoven media (see www.welcron.com/_ENG/html/material01.asp) or W.L. Gore expanded polytetrafluoroethylene (e-PTFE) air filter media, or high efficiency nonwoven, or porous filter media provided by vendors such as Welcron, W.L. Gore, Donaldson, eSpin Technologies, Hollingsworth & Vose, and Hills Inc.).

Other materials that could be used in the high efficiency air filtration media that behave like e-PTFE or the other medium above. The optional wire mesh layer shown in FIG. 4 may be used as a support for depositing nanofibers to form a high efficiency air filtration media (as described above). Indeed, in one embodiment, the fibers are deposited onto the wire mesh with no intervening materials. In one embodiment, the wire mesh when present can be used to provide electrical power for the LEDs associated with the optical fibers. The optional wire mesh layer may extend beyond the media assembly and can be made from a coarse metal (e.g., nickel, steel, coated steel, tungsten) grid.

In one embodiment of the invention, the high efficiency media comprises for the particle capture layer 106 a nanofiber mat. In one embodiment of the invention, the high efficiency nanofiber mat comprises patterned nanofibers formed onto a base dielectric coarse filtration material (hereinafter "base material") supported by a wire mesh having macroscopic openings. As used herein, patterned nanofibers are fibers formed on the base material in compliance with a predefined pattern of the wire mesh and thereby forming an organization and orientation of the fibers above the wire mesh. The patterned nanofibers can be formed on a wire mesh as described in U.S. Pat. No. 10,188,973. This patterning can include simple patterns as well as nested or complex patterns. The following procedures are suitable for production of a nanofiber mat useful in the present invention, wherein the nanofiber mat comprises a) base having openings for fluid flow there through and a filtration medium, and b) a plurality of patterned nanofibers formed on the base. The nanofiber mat as a filtration medium itself would preferably have a figure of merit greater than 30 $kPa^{-1}$, where the figure of merit is given by $-Log (Pt)/\Delta P$, where Pt is the fractional penetration of a specific aerosol particle diameter and $\Delta P$ is a pressure drop in kPa across the filtration medium corresponding to a face velocity of 5.3 cm/s and particle size of 0.3 microns. A filter media with high efficiency and high FoM is able to provide a high level of protection with minimal burden (i.e., filter is easier to breathe through and/or it can be a smaller size). However, lower figures of merit would not make the present air filtration media with integrated disinfection unworkable, and in one embodiment the present invention is not limited to using nanometer sized fibers in the fiber mat of the air filtration media with integrated disinfection.

Figure 2:
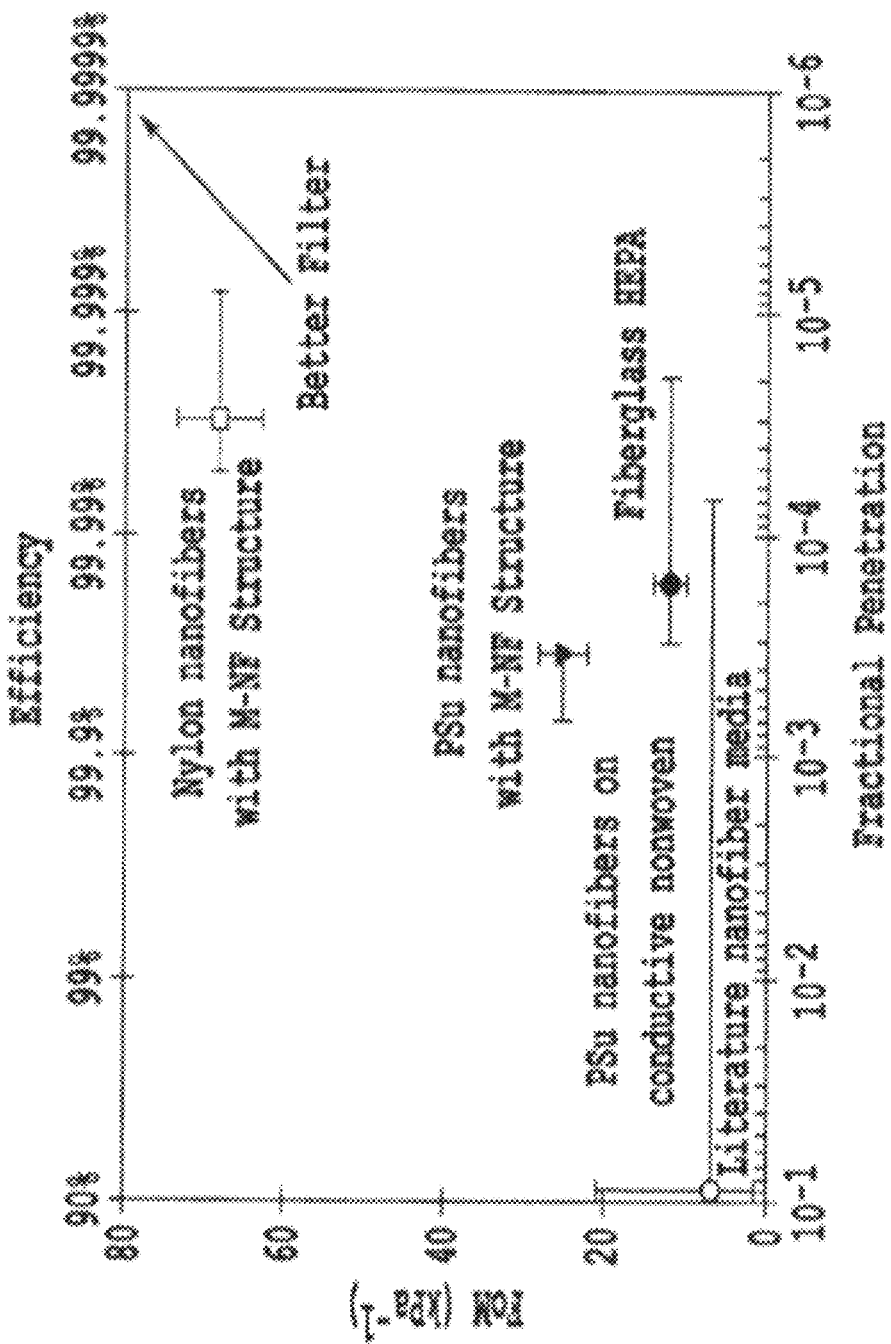
FIG. 2 is a graph comparing filtration performance for various filter medias including the nano-fiber filters of the present invention.

A comparison of different nanofiber filter technologies is shown in a plot of FoM versus Pt in FIG. 2. Specifically, FIG. 2 is a graph comparing filtration performance for various filter medias including the nano-fiber filters of the present invention. Performance measured with 0.3 μm particles at 5.33 cm/s. Data points represent average values of collected data sets. The literature data are from a range of materials and fabrication processes with the error bars representing the full range of values observed in the published literature. Error bars on all other materials are for a standard deviation of a data set.

This plot in FIG. 2 is in essence the effectiveness of filtration obtained for the level of filtration protection (efficiency of filtration) provided. Data for the integrated metal-mesh fiber structure are compared with conventional nanofiber and fiberglass filter media. Data from "nylon-based nanofiber media" and "polysulfone (PSu)-based nanofiber media" are given as well as the average and standard deviation for a large number of samples made (more than 20). "Fiberglass" data are average and standard deviation for a variety of commercial samples. "PSu nanofibers on conductive nonwoven" are samples deposited onto a nonwoven substrate coated with conductive graphite paint (Aerodag). These materials offer no statistically significant improvement over conventional fiberglass filter media. The "literature nanofiber media" are a wide variety of materials reported in the literature with the error bars representing the full range of values observed rather than a standard deviation of samples made via a single fabrication process. For the plot of FIG. 2, the further to the top-right of the plot, the better is the filtration performance of the material.

Figure 3:
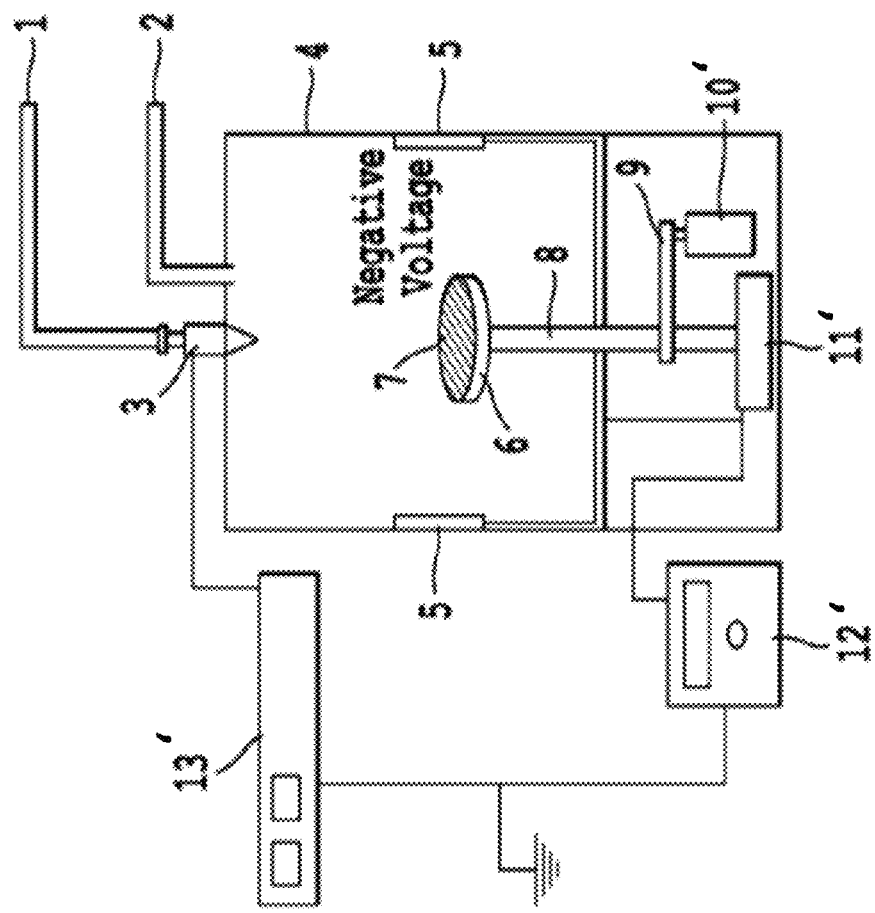
FIG. 3 is a depiction of one configuration for the patterned deposition of electrospun nanofibers onto substrates such as insulating nonwovens.

One configuration for patterned deposition of electrospun nanofibers onto a flexible, light-weight nonwoven substrate is shown in FIG. 3. The components depicted in FIG. 3 are a syringe pump/polymer solution delivery system 1, carbon dioxide or other electronegative gas supply 2 with temperature and RH control, spinneret 3, enclosure 4 for safety and environmental control, optional auxiliary electrodes 5 with negative potential, metal or conductive pattern 6, substrate 7 (woven, nonwoven, or similar) to deposit fibers onto, vacuum or vent line 8, insulated drive belt 9 to provide rotation or substrate movement, electric motor 10' to drive rotation or positioning, connections 11' for negative voltage, negative high voltage supply 12', and positive high voltage supply 13'.

For production of a patterned nanofiber mat, a negative bias voltage is applied directly to the wire mesh. In some embodiments, voltages can range from a few hundred to up to ten thousand volts, or more depending upon the materials and needed processing conditions. Positively charged nanofibers are highly attracted to the negative bias on the grid and began to deposit onto the base material in a rapidly growing pattern. The result is that, during the spinning of the nanofibers, the fibers take the same pattern of the wire mesh underneath.

Conventional nanofiber electrospinning methods rely on a high positive voltage (+20 kV to +40 kV or higher) applied to a needle (i.e., spinneret) or other device that holds or manages the liquid solution to be spun into nanofibers. The target area (or substrate) for the spun nanofibers has to be at a ground potential (or significantly lower potential than the spinneret) in order to attract the highly positively charged fibers. These charged fibers land onto the grounded surface and form a layer of fibers (also called a mat). Typically, the fibers collect in random orientations forming a nonwoven fibrous mat on top of the substrate. With current methods the substrate is usually made of conductive materials (e.g., metal mesh), or materials with a conductive coating such as carbon paint. Alternately, a thin, minimally-insulating substrate, such as a light-weight nonwoven backing, is placed on top of a grounded target and then the fibers are deposited onto the substrate.

In contrast, for production of a patterned nanofiber mat, a patterned grid mechanism (e.g., the wire mesh shown in FIG. 3) is placed directly underneath the substrate. A non-conductive material including woven or nonwoven materials and possibly even membranes and other materials that are modest electrical insulators can be placed on the grid mechanism. A negative bias voltage is applied directly to the patterned grid that is underneath the substrate.

While described below with regard to patterned fiber production, this invention for an air filtration media with integrated disinfection capability is not limited to those structures although the patterned fiber mats are preferred. While illustrated below with a Psu polymer, other polymeric materials can be used in a similar manner to that discussed below to obtain a high figure of merit filtration medium. In the illustrated embodiment below, a polymer solution containing PSu polymer in a solvent (using standard formulations) is fed to a 30 G needle. $CO_2$ gas mixed with water vapor and heated to 30° C. flows over the syringe and syringe needle. Additional relative humidity (RH) controlled $CO_2$ gas is injected into the electrospinning chamber. A positive power supply is connected to the spinneret and shares a common earth ground with a negative power supply connected to the patterned grid used to drive the patterned deposition of the nanofibers. The nonwoven substrate is mounted on a frame above the patterned grid.

Further, the grid can be in contact with or with a small air gap between the substrate and the grid. Auxiliary electrodes can be used that are connected to the negative power supply to aid in broadening the overall electric field to provide for even dispersion of fibers over the substrate. The substrate can be rotated relative to the spinneret to improve fiber dispersion. The RH- and temperature-controlled $CO_2$ gas flows through the substrate and out the chamber venting system. This flow of gas may help dry the fibers and more generally controls the drying rate.

Using the patterned deposition method (which is preferred but not necessarily needed for this invention), filters were electrospun with high FoMs and high efficiencies (low Pt). Samples with the following performance metrics were made: 1) a FoM of 45.7 $kPa^{-1}$ and a Pt of $2.34\times10^{-4}$, 2) a FoM of 44.1 $kPa^{-1}$ and a Pt of $6.99\times10^{-4}$. Performance was measured with 0.3 μm particles at 5.33 cm/s. In general, the particle capture layer 106 shown in FIG. 1B may have a figure of merit between 20 $kPa^{-1}$ and 40 $kPa^{-1}$ or between 40 $kPa^{-1}$ and 60 $kPa^{-1}$, or between 60 $kPa^{-1}$ and 70 $kPa^{-1}$, or between 70 $kPa^{-1}$ and 80 $kPa^{-1}$.

Figure 4:
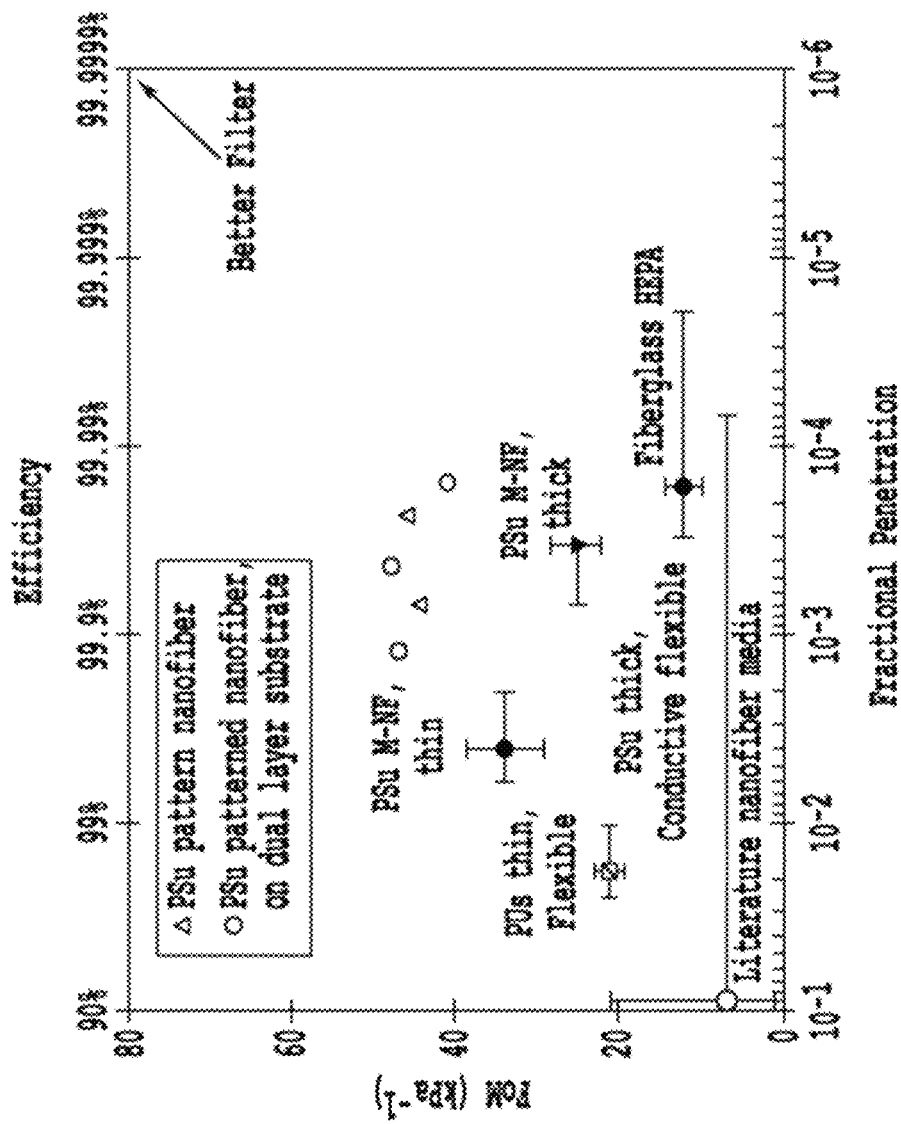
FIG. 4 is a graph comparing patterned nanofiber media of the present invention to nanofiber media without patterning and to nanofiber media on a metal mesh.

FIG. 4 compares the results of the patterned deposition of nanofibers onto insulating nonwovens with other fibrous media. Specifically, FIG. 4 is a graph comparing patterned nanofiber media of the present invention to nanofiber media without patterning and to nanofiber media on a metal mesh. In FIG. 3, the patterned nanofiber media are compared to an integrated metal-mesh fiber structure (M-NF Filter structure) and to nanofibers deposited onto flexible nonwoven substrates without patterning.

The present invention can utilize filtration medium with a large range of figures of merit but with preferred values of figures of merit being 30 $kPa^{-1}$ to 60 $kPa^{-1}$ or higher. . In various embodiments, the figures of merit can range from 1 $kPa^{-1}$ to 60 $kPa^{-1}$. In various embodiments, the figures of merit can range from 10 $kPa^{-1}$ to 50 $kPa^{-1}$. Intermediate range values can be used.

Using this process of a conductive patterned grid (or surface) behind the substrate with deposition of charged fibers onto a substrate, a variety of fiber deposition configurations are possible. With the present invention, the metal mesh is used to create the pattern in conjunction with the use of a negative electric potential applied to the mesh. Accordingly, the nanofibers can be deposited onto a flexible substrate (for example a thin nonwoven that is not inherently conductive).

The electrospinning conditions (choice of polymer, electric field conditions, controlled environment conditions with for example CO gas flow) can be the same or similar to those described in the '973 patent referenced above describing techniques for formation of an integrated metal-mesh fiber structure. For example, a mixture of dry and wetted (via bubbling through DI water) $CO_2$ can be used to obtain an RH in the range of 26 to 38%. A 21 wt % PSu (Udel P3500 LCD by Solvay Advanced Polymers) in dimethylacetamide (DMAC) with the 0.2 wt. % TBAC can be used as the polymer solution. This polymer solution can be spun from a 30G (ID⁻0.152 mm) stainless steel needle with a flow rate of 0.05 ml/hr, a gap of 25.4 cm, an applied potential of 29.5 kV DC, and a $CO_2$ gas jacket flow rate of 8 L/min.

In addition to electrospinning, other techniques can be used for production of fibers and/or nanofibers for use in the particle collector layers and in the surrounding radiation scattering and diffusion layers (described below). These techniques include electroblown spinning as described in U.S. Pat. No. 7,585,451 (the entire contents of which are incorporated by reference), centrifugal spinning as described in U.S. Pat. Appl. Publ. No. 2009/0160099 (the entire contents of which are incorporated by reference), force spinning as described in U.S. Pat. Appl. Publ. No. 2009/02329020 (the entire contents of which are incorporated by reference), and rotary spinning as described in U.S. Pat. Appl. Publ. No. 2010/0247908 (the entire contents of which are incorporated by reference).

For example, one alternative method to fabricate nanofibers and/or fibers for use in this invention is through the process of centrifugal spinning or a closely related process called Force™ spinning. The details of centrifugal spinning are described in U.S. Pat. Appl. Publ. No. 2009/0160099 (the entire contents of which are incorporated by reference), the details of force spinning are described in U.S. Pat. Appl. Publ. No. 2009/02329020 (the entire contents of which are incorporated by reference), and the details of rotary spinning as described in U.S. Pat. Appl. Publ. No. 2010/0247908 (the entire contents of which are incorporated by reference). In these methods, shear forces arising from the high speed ejection of the polymer from a rotating spinnerette thin the film down to the nanofiber range. The nanofibers can be collected in layers either as they are ejected from the rotating spinnerette or formed into a mat using conventional means including air and electrostatic charging. Centrifugal spinning can be used on either polymer solutions (typical polymer concentration of 10% to 50%) or polymer melts. When polymer solutions are used in the nanofiber spinning process, common organic solvents including but not limited to formic acid, toluene, dimethyl formamide may be used. Common polymer nanofibers fabricated using centrifugal spinning include polyethylene, polypropylene, polyethylene terephthalate, polybutyleneterephthalate, nylon, polyimide, polyetherimide, polysulfone, polymethyl methacrylate, and blends thereof.

In making a nanofiber radiation scattering diffusion layer (i.e., a reflector) or a fiber collection layer for use in this invention, centrifugal spinning or FORCE spinning can be used. First, the spinning solution must be of the appropriate composition and viscosity to achieve the intended average fiber diameter (<500 nm). For centrifugal spinning, this can be achieved either through the use of a polymer solution (concentrations ranging from 10% to 50%) or a polymer melt heated to a sufficient temperature to reduce its viscosity. The solution composition in conjunction with the rotary rate of the centrifugal spinerette control the average fiber diameter of the end product. More viscous solutions require higher rotary spinning rates to achieve a fiber diameter <500 nm, compared to less viscous solutions. However, more viscous solutions will typically have a higher throughput and be able to produce more material in a given time frame. Second, the centrifugal spinning system is designed to produce sufficient fiber densities to achieve the bulk substrate properties as measured by mean flow pore diameter and bubble point required to achieve high reflectance across the entire nanofiber reflector substrate. In a centrifugal spinning system for producing the large amounts of material needed for lighting, this is typically achieved with a multiple spinerette architecture that can produce uniform fiber densities across a broad area. If the fiber density is too low, the substrate exhibits higher transmittance than desired. If the fiber density is too low, the reflectance of the material will decrease. Third, the collection belt for the nanofiber substrate is operated at a sufficient speed to ensure that the substrate basis weight remains below 40 gsm, more preferably below 30 gsm, and most preferably below 20 gsm. If the belt speed is operated at too high a rate, then sub-optimal basis weight is obtained. If the belt speed to too high, then excess material is incorporated into the substrate, increasing costs and decreasing flexibility, with significantly improving reflectance.

Another alternative method to fabricate nanofibers and/or fibers for use in this invention is through nanofiber melt-blowing. In this process, polymer resin is heated above its melting point and then forced under high through a specially designed fiber extrusion head to produce fibers in the 300 nm to >1,000 nm range. The combination of fiber extrusion head and air velocity and direction are adjusted to achieve AFD values <500 nm, as required for high reflectance substrates. The fibers are typically collected on a belt using either air knives or electrostatic charge accumulation. Common polymer nanofibers fabricated using melt-blowing include polyethylene, polypropylene, polyethylene terephthalate, polybutyleneterephthalate, and similar polyolefin and polyester materials.

The nanofiber and fiber structures described herein can also be fabricated using a roll-to-roll spinning process as in an Elmarco Nanospider tool, as described in U.S. Pat. Appl. Publ. Nos. 2009/0148547 and 2010/0034914, the entire contents of these patent documents incorporated by reference herein. As described therein, production of nanofibers through electrostatic spinning of polymer solutions occurs by way of a spinning electrode which rotates around its longitudinal axis and having spinning elements positioned uniformly along the circumference of end faces which are subsequently plunged under the level of polymer solution in the reservoir of polymer solution. Due to the physical properties of the polymer solution and the spinning electrode, the spinning elements emerge from the reservoir covered by the polymer solution. Having emerged, the spinning elements with polymer solution subsequently approach to a collecting electrode, which is grounded or connected to an opposite voltage source other than that of the spinning elements of the spinning electrode. In the moment, when the spinning element approaches sufficiently to the collecting electrode, between it and the collecting electrode as a result of difference of their electric potentials, there is created a sufficiently strong electric field, which along the whole length of the spinning element initiates the spinning process. During the spinning process the polymer nanofibers are created from the polymer solution on surface of the spinning element, which through the action of force of electrostatic field move towards the collecting electrode.

In this roll-to-roll process, the spinning element remains in a position suitable for spinning of the polymer solution on its surface only for a certain time interval. After expiration of this time interval, the spinning element is moved away from vicinity of the collecting electrode and again plunged into the polymer solution in the reservoir of polymer solution. Meanwhile, other spinning elements containing the polymer solution for spinning on their surface are in position to electrospin, permitting a continuous production of nanofibers in this roll-to-roll process.

Various polymers available for production of nanofibers (or fibers) of the present invention include, but are not limited to, acrylonitrile/butadiene copolymer, cellulose, cellulose acetate, chitosan, collagen, DNA, fibrinogen, fibronectin, nylon, poly(acrylic acid), poly(chloro styrene), poly(dimethyl siloxane), poly(ether imide), poly(ether sulfone), poly(ethyl acrylate), poly(ethyl vinyl acetate), poly (ethyl-co-vinyl acetate), poly(ethylene oxide), poly(ethylene terephthalate), poly(lactic acid-co-glycolic acid), poly (methacrylic acid) salt, poly(methyl methacrylate), poly (methyl styrene), poly(styrene sulfonic acid) salt, poly(styrene sulfonyl fluoride), poly(styrene-co-acrylonitrile), poly (styrene-co-butadiene), poly(styrene-co-divinyl benzene), poly(vinyl acetate), poly(vinyl alcohol), poly(vinyl chloride), poly(vinylidene fluoride), polyacrylamide, polyacrylonitrile, polyamide, polyaniline, polybenzimidazole, polycaprolactone, polycarbonate, poly(dimethylsiloxane-co-polyethyleneoxide), poly(etheretherketone), polyethylene, polyethyleneimine, polyimide, polyisoprene, polylactide, polypropylene, polystyrene, polysulfone, polyurethane, poly (vinylpyrrolidone), poly(2-hydroxy ethyl methacrylate) (PHEMA), gelatin, proteins, SEBS copolymer, silk (natural or synthetically derived), and styrene/isoprene copolymer.

Additionally, polymer blends can also be produced as long as the two or more polymers are soluble in a common solvent or mixed solvent system. A few examples would be: poly(vinylidene fluoride)-blend-poly(methyl methacrylate), polystyrene-blend-poly(vinylmethylether), poly(methyl methacrylate)-blend-poly(ethyleneoxide), poly(hydroxypropyl methacrylate)-blend poly(vinylpyrrolidone), poly(hydroxybutyrate)-blend-poly(ethylene oxide), protein blend-polyethyleneoxide, polylactide-blend-polyvinylpyrrolidone, polystyrene-blend-polyester, polyester-blend-poly(hydroxyethyl methacrylate), poly(ethylene oxide)-blend poly (methyl methacrylate), poly(hydroxystyrene)-blend-poly (ethylene oxide).

Other embodiments of the present invention include the use of polymers that are resistant to UV degradation which include for example cyclic olefin copolymers (COC) such as TOPAS® (see topas.com/uv-transparency), PTFE, e-PTFE, polyvinylidene fluoride, fluorinated ethylene propylene, polyether ether ketone (PEEK), quartz, and other mineral materials.

The thickness of a suitable nanofiber mat can vary from about 0.10 μm (100 nm) to 500 μm or beyond if needed to millimeter size, where most filters had an average mat thickness in the range of 2 to 5 microns. The average mat thickness numbers represent the average thickness of the total nanofiber mat in a filter. Alternately the mat thickness can be defined as layers of nanofibers with the thickness including from 4 to 4000 layers where 4 to 400, or 5 to 100, or 2 to 15 layers were typical in various embodiments.

Regardless of fiber production technique or the type of fiber used, in one embodiment of the invention, additives (e.g., white pigments such as titanium oxide) may be added to promote diffuse reflection of electromagnetic radiation and for germicidal purposed. Additives included with the fiber structures or provided as a coating throughout or on a part of a fibrous medium (or fabric) of the particle capture layer 106 or the optical diffusion layers 104, 112 could be used to destroy viruses and other microbes on the product surfaces (e.g., silver ionic coating or imbedded particles are well known anti-microbial additives to textiles). These additives could also mitigate microbial growth on surfaces within the apparatus.

Returning to FIG. 1B, the optically active layer 108 shown in FIG. 1B is formed of a network of coarse optical fibers used to introduce electromagnetic radiation (e.g., UV radiation) into the structure. The layer is comprised of a LED coupled to or contained within one or more optical fibers that have been modified to emit electromagnetic radiation in a diffuse of directed manner. Electrical leads to the LEDs extend beyond the media assembly and can be connected to a battery or power supply to operate the LEDs. The coarse optical fibers may comprise optical waveguides made of a material that is non-absorbing to the electromagnetic radiation from the LEDs. Examples of such material include fibers made from cyclic olefin copolymers (COC) such as TOPAS® (see topas.com/uv-transparency), polyvinylidene fluoride (PVDF), fluorinated ethylene propylene (FEP), polyether ether ketone (PEEK), quartz, and other mineral materials. The fibers may be cladded to promote total internal reflection (e.g., various waveguide modes) and the cladding can be modified through the incorporation of nanomaterials or etching to promote the emission of electromagnetic radiation at select locations or along the length of the fiber. V Optical fiber systems are known to be efficient means to transport optical signals over large distances. Optical fiber systems include an electromagnetic radiation source (e.g., LED, micro-LED, laser) that is optically coupled to one or more fibers. The properties of the fiber (e.g., diameter, composition, cladding material) are chosen such that the electromagnetic radiation signal can propagate for extended distances through total internal reflection and arrive at the distal end of the fiber with minimal loss.

FIG. 5 is a schematic depiction of a fiber optic 200 with Bragg diffraction gratings 210 etched into the surface to permit electromagnetic radiation "leakage" at select points. In this embodiment, the surface of an optical fiber is modified at discrete locations (or continuously) to allow a small fraction of the transmitted electromagnetic radiation to exit the fiber at that point or progressively along the entire length. Electromagnetic radiation emitted from the fiber can be omnidirectional, resulting in a diffuse electromagnetic radiation source. Methods of fiber modification to achieve the emission of omnidirectional electromagnetic radiation along the fiber length include adding nanomaterials to the fiber cladding can be used (see www.corning.com/worldwide/en/innovation/the-glass-age/science-of-glass/how-it-works-light-diffusing-fiber.html describing the Corning® product Fibrance®, a silica fiber infused with optical nanostructures whereby, when light or radiation hits these nanostructures, the fiber evenly emits or diffuses the light or radiation out of the sides. Similarly, surface etchings on fiber cladding as shown in FIG. 1 can be used (see www.fiber-core.com/product-category/fiber-bragg-grating-(fbg)?gclid=CjwKCAjw95D0BRBFEiwAcO1KDIDOZimfXYcBs2CXC3p7q13kI1hzhP4CrG eCuwaQY1Y51YxYJCdVwRoCGvIQAvD_BwE).

A more directional "leak" of electromagnetic radiation from an optical fiber can be achieved by applying a condensed material (e.g., polymer) along at a length of the optical fiber at bends in the fiber (at www.youtube.com/watch?v=MSdpRzBbR2E&t=3s). Suitable condensed materials for the present invention include (but are not limited to) the following commercial products: Epotek 305 (transparent to below 260 nm) Norland NOA88 (transparent to 300 nm), Epoxies Etc. 20-3302 (transparent to 300 nm), Master Bond EP3OLV or EP29LPSP ("optically clear"). For those "optically clear" and transparent to 300 nm materials, relatively thin layers should be used to minimize absorption of UV radiation.

In addition, the optical fiber may have LEDs embedded along its length to create LED fibers such as those described by U.S. Patent Application 2018/0039036 (the entire contents of each of which are incorporated herein by reference). In the '036 patent application, there is provided a fiber including a fiber body with a fiber body material having a longitudinal axis along a fiber body length. A plurality of devices (e.g., LEDs) is disposed as a linear sequence of devices within the fiber body. Each device includes at least one electrical contact pad. At least one electrical conductor is disposed within the fiber body.

Here, in this invention, ultraviolet light emitting diode UVLED devices (which can emit UV radiation) can be placed in the milled pockets on the fiber body, with the anodes of all devices oriented in the same direction, which was marked on the preform. Additional information on such LED fibers is provided at www.ll.mit.edu/news/fibers-embedded-electronics-are-putting-fabrics-work. Here, in the present invention, electronic fibers (to contain the UVLEDs) start out as a block of polycarbonate (PC) called a preform. Other preform materials include but are not limited to COC (e.g., Topas) or silica. The UVLEDs are embedded down the center of the preform, and copper wire is fed into small channels running down the preform on both sides of the diodes. Wire mesh layer 110 may be used to power the embedded UVLEDs in this construction. The preform is then heated up at the top of a draw tower, which pulls the warm, taffy-like substance into a long fiber strand. This stretching of the preform spaces out the embedded UVLEDS and forces the wires into contact with them. As a result, hundreds of UVLEDs can become electrically connected in parallel inside a single fiber thin enough to be threaded through a needle.

In one embodiment of the present invention, there can be multiple optically active layers 108. For example, a first optically active layer could exist to one side of the particle capture layer 106, and another optically active layer could exist to the opposite side of the particle capture layer 106. In one embodiment, the optically active layer 110 (and a battery for powering the optically active layer) may be removable from and/or installable in a housing containing the first and second electromagnetic radiation scattering and diffuser layers 104 and 112, the particle capture layer 106, and the optional wire mesh layer 108.

In one embodiment of the present invention, the first and second electromagnetic radiation scattering and diffuser layers 104 and 112, the particle capture layer 106, the optional wire mesh layer 108, the optically active layer 110 can provide the component of a garment. In this embodiment, the garment could be part of a head and/or neck covering or could be part of sleeve extending for example past the wrist and covering skin not covered by gloves. As pathogens diffuse migrate through the coverings, the optically active layer 110 can generate UV radiation for disinfection of the pathogens.

Exemplary Respirator

In one embodiment of the present invention, included in filter frame 38 shown in FIG. 1B are the first and second electromagnetic radiation scattering and diffuser layers 104 and 112, the particle capture layer 106, the optically active layer 110, and (as depicted) the wire mesh layer 108 (which is optional). In another embodiment, included in filter frame 38 are the inner and outer shell layers 102, 114, the first and second electromagnetic radiation scattering and diffuser layers 104 and 112, the particle capture layer 106, the optically active layer 110, and the wire mesh layer 108 (which is optional). The inner and outer shell layers 102, 114 in this invention (besides support and coarse filtration) can function as an optical stop for UV radiation so that it does not escape outside. In another embodiment, included in filter frame 38 are the particle capture layer 106, the optically active layer 110, and the wire mesh layer 108 (which is optional). In this embodiment, the respirator housing acts to stop UV radiation from escaping outside.

Figure 6B:
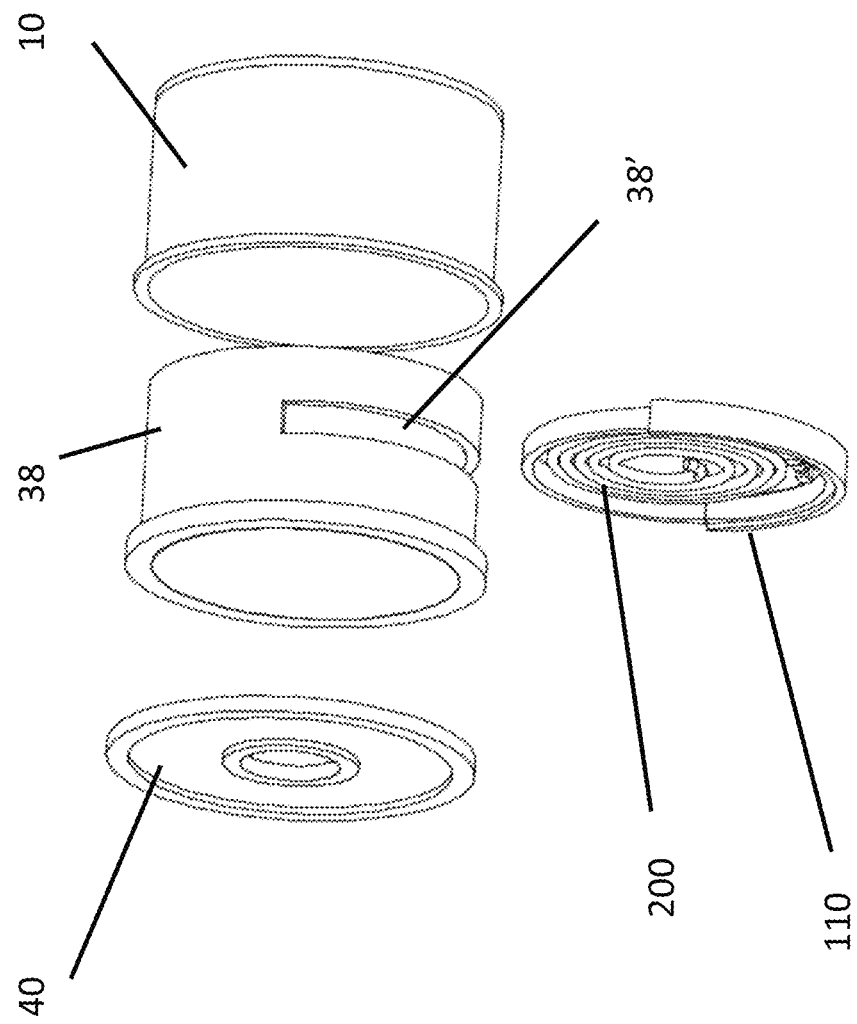
FIG. 6B is a view of the respirator cartridge shown in FIG. 1 showing a slot for insertion of an optically active layer.

As noted above, in one embodiment, the optically active layer 110 (and a battery for powering the optically active layer) may be removable from and/or installable in a housing (e.g., filter frame 38). As shown in FIGS. 6A and 6B, the optically active layer 110 including fiber optic 200 (as described above, but here wound into a spiral pattern) can be inserted through slot 38' in the filter frame 38. By having this as a removable piece, the UVLEDs of fiber optic 200 can be re-used whenever the other elements inside filter frame 38 such as the first and second electromagnetic radiation scattering and diffuser layers 104 and 112, the particle capture layer 106, and the wire mesh layer 108 have to be discarded.

Figure 8:
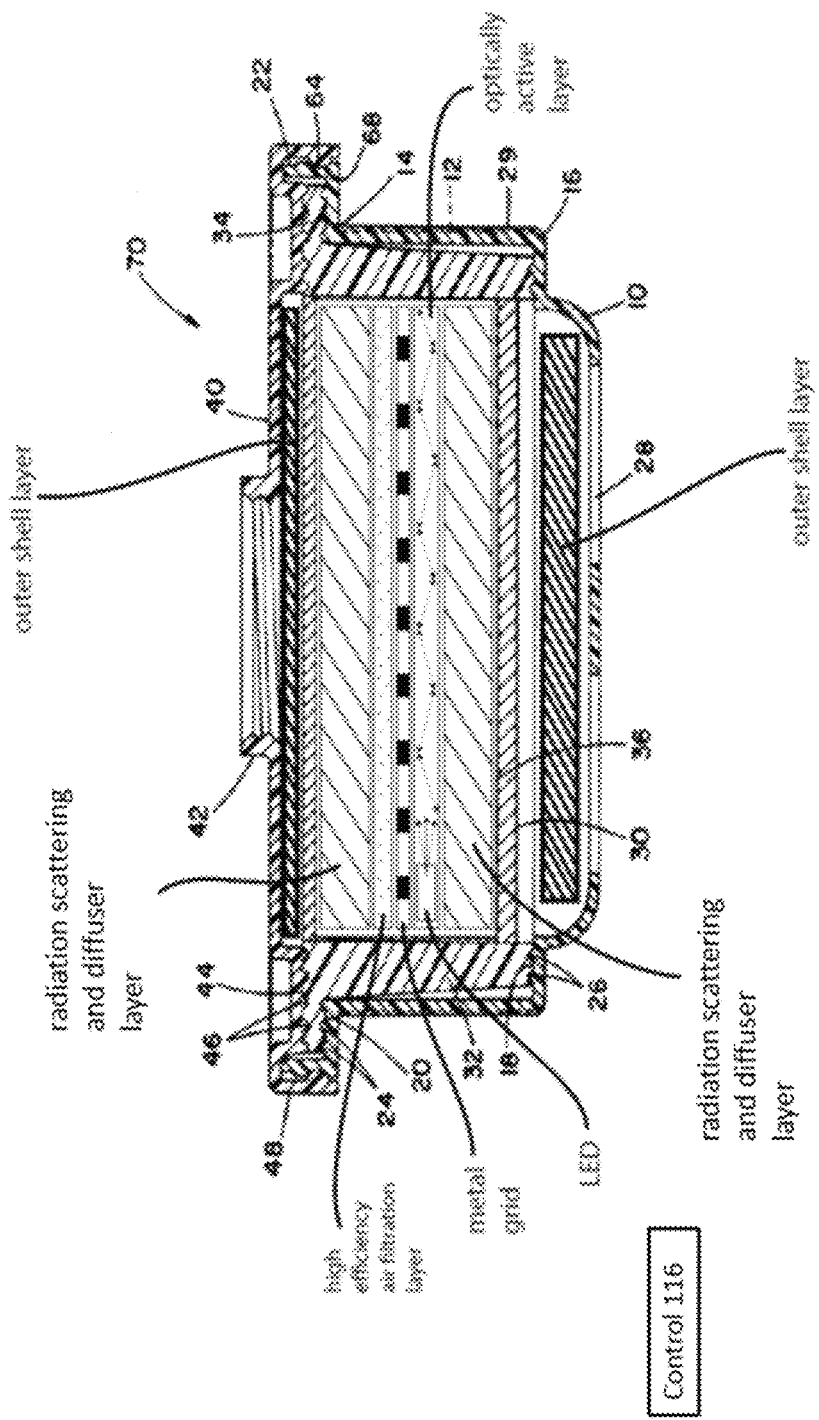
FIG. 8 is a cross-sectional view of the respirator cartridge shown in FIG. 1 taken generally along the line 3--3 in FIG. 7.
Figure 9:
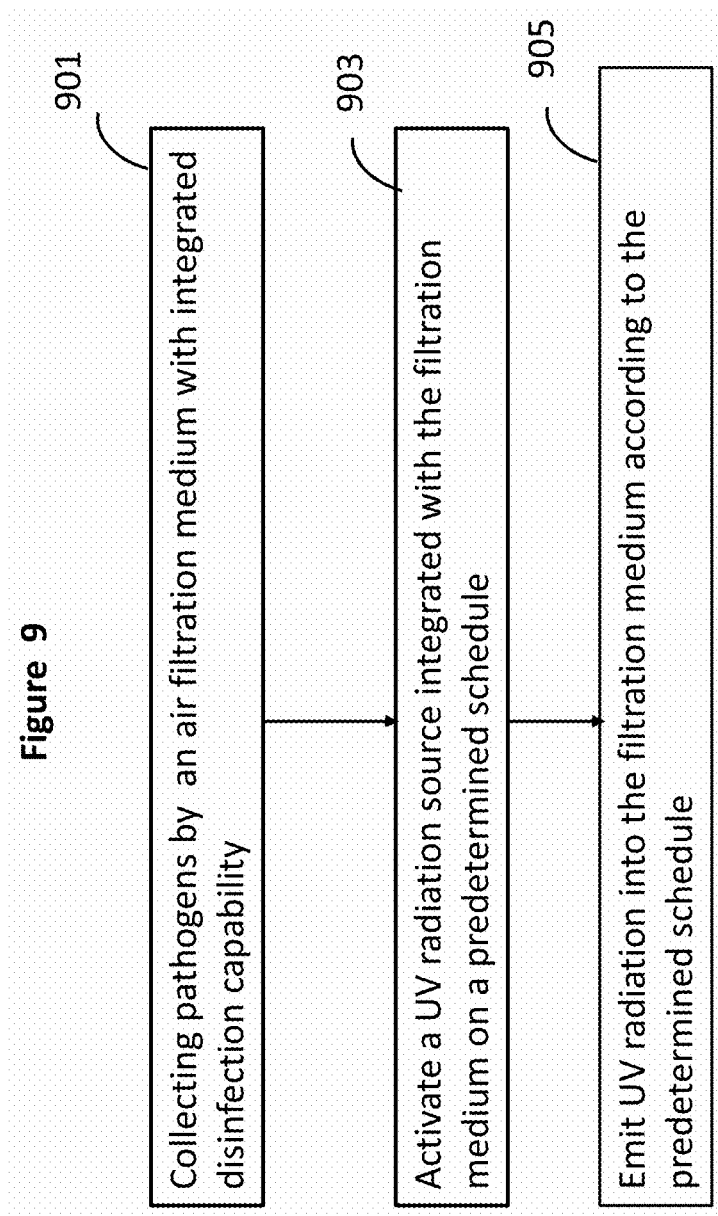
FIG. 9 is a flowchart detailing a method of the present invention for sterilizing pathogens.

When cartridge is assembled (as shown in the side view of FIG. 7 and the sectional view of FIG. 8), cover 40 extends over housing 10 and filter 30. A peripheral sealing surface 44 of cover is disposed against sealing lip 34 of filter frame and an outer peripheral wall 48 is disposed outwardly of and adjacent to annular peripheral wall 22 of housing. Respirator latch 42 is located on cover 40 although, as stated earlier, it could be located on the other end of cartridge 70, depending upon the overall design of the cartridge.

Means for sealing cartridge 70 are provided by filter frame 32 and concentric sealing rings 24,26,46 on sealing surfaces 20,44 and on filter support surface 18. Filter 30 is first sealed by a series of concentric sealing rings 24,46 on sealing surfaces 20,44 providing repetitive gasketing and sealing when sealing lip 34 is compressed between sealing surfaces 20,44. Sealing rings on housing 24 correspond to sealing rings on cover 46 to provide localized pressure which concentrates force over a smaller area, enhancing the seal integrity. An additional sealing location is provided by concentric sealing rings 26 on filter support surface 18 when bottom of filter frame 38 is compressed against filter support surface 18.

Filter frame 32 is preferably spin molded from a resilient plastic material of such a durometer that it can be deformed to provide for gasketing and sealing. In the preferred embodiment, filter frame 32 is molded from polyurethane with a durometer of less than 50 Shore A hardness. Housing 10 and cover 40 are made of injection-molded plastic sufficiently hard t deform filter frame 32 when cover 40 is releasably connected to housing 10.

In Use Disinfection

The disinfection of the air filtration media described above is advantageous since it allows the filtration media to be reused with a greatly reduced risk of the trapped biological material becoming resuspended and inhaled by humans. A second advantage is that a majority if not all of the captured biological material can be destroyed with the germicidal radiation eliminating the safety and handling issues associated with removing and disposing of spent personal protective equipment.

The disinfection function of the subject invention can be activated by supplying appropriate electrical power to the LED(s) that provide the actinic/germicidal radiation. This process can be done in situ while masks and respirators containing the filtration media are being worn, and the activation can be either continuous or pulsed at a desired duty cycle through a battery and control circuit. This process can also be done in situ for flat or pleated filtration media containing the subject injection using a control circuit and either a continuous or pulsed waveform to operate the LEDs at a desired duty cycle. The power source for the flat or pleated media can be either a battery, an electrical bus provided by the HVAC system, or an external power supply.

The electromagnetic radiation used for the device can be chosen to provide a high kill rate of any biological materials trapped on the high efficiency air filter media. The wavelength of the LEDs/ microLEDs used in this device can range from UV-C (200-280 nm) up to blue (~450 nm), with the UV-C radiation providing the highest probability for killing biological materials (see D. H. Sliney, "Introduction to Ultraviolet Germicidal Irradiation (UVGI) and Visible Lighting Disinfection. Part 1: Introduction", IES webinar, Sep. 19, 2019 community.ies.org/events/event-description?CalendarEventKey=58fd1791-78e7-420f-b91c-7ae9d36668c9&Home=%2fevents%2fevent-description and see International Ultraviolet Association Fact Sheet on UV Disinfection for COVID-19 www.iuva.org/COVID-19).

Packaged LEDs emitting at such wavelengths are provided by multiple manufacturers including Nichia (e.g., NCSU334A product with $\lambda_p$ at 280 nm see nichia.co.jp/en/product/uvled.html) and Osram www.osram.com/os/press/press-releases/unique_project_for_developing_mass_market_uv_leds_for_disinfection.jsp). Unpackaged LEDs can also be obtained from the manufacturers listed above or from distributors such as III-V Compounds Inc. with offices in New York, NY (see www.35compounds.com/home.html).

In one embodiment of the present invention, the LEDs are either coupled to an optical fiber configured for emitting diffuse electromagnetic radiation (as shown in FIG. 5) or incorporated directly into the high efficiency air filtration medium to create a source of actinic and/or germicidal electromagnetic radiation in close proximity to the particle capture layer such as a nanofiber filter. Since the electromagnetic radiation scattering and diffusing layer(s) redirect the actinic/germicidal radiation back toward the high efficiency air filtration media, a minimal amount of electromagnetic radiation is expected to escape the inner layers of the media. To prevent further escape of electromagnetic radiation, the shell layers can incorporate pigments (e.g., carbon black, $TiO_2$) that are known to be highly absorptive of the electromagnetic radiation produced within the structure.

Alternatively, the air filtration media described in this invention can be disinfected at a location remote from its use site. The multi-layer air filtration media is removed to the location for disinfection, and one or more media are connected to a source of electrical power at the appropriate voltage and current (e.g., battery, power supply). A control 116 as shown in FIG. 8 may be used to regulate operation of the LEDs, and the LEDs can be operated continuously or on a duty cycle. Continuous operation would have the added advantage of generating heat (through inefficiencies in the LEDs and the electrical circuit) which may aid in the disinfection process. Pulsed operation is likely to be beneficial when a battery is used to increase battery life. In one embodiment, control 116 may be a simple switch on the filtration unit which is manually turned on and manually turned off, In one embodiment, control 116 may be a switch integrated into the filtration unit which is switched on by a flow sensor detecting air flow through the filtration unit. In one embodiment, control 116 may be a switch which is switched on by contact switch or sensor sensing contact of the filtration unit to an opposing surface such as for example a respirator sensing that it has been secured to a human face. In one embodiment, control 116 may be remote or detached from the filtration unit and a broadcast signal from control 116 activates a switch on the filtration medium. The present invention in this embodiment can use a variety of signals including but not limited to radio frequency, laser, infrared, and acoustic signals. As detailed later, the signals may be communication, power, data, or energy signals, which may communicate information, power, or energy from a first system, device, component, module, or sub-module (control 116) to a second system, device, component, module, or sub-module (filtration unit switch circuitry) along a signal path between the first and second system, device, component, module, or sub-module.

Currently any air filtration media that is potentially subjected to biohazards (e.g., germs, viruses, biological agents) must be carefully handled and disposed of as biohazardous waste. This increases the costs associated with disposal of such materials. The subject invention would allow any biological material contained within the structure to be deactivated, which would greatly simplify the disposal of the material and reduce disposal costs.

Control

It will be understood that the control 116 schematically illustrated in FIG. 8 may also be representative of one or more types of user input devices (e.g., keypad, touch screen, mouse, and the like) or user output devices (e.g., display screen, printer, visual indicators or alerts, audible indicators or alerts, and the like). Control 116 may have a graphical user interface (GUI) controlled by software for display by an output device, and one or more devices for loading media readable by the controller 116 (e.g., logic instructions embodied in software, data, and the like). The controller 116 may include an operating system (e.g., Microsoft Windows® software) for controlling and managing various functions thereof.

FIG. 9 is a flowchart detailing a method of the present invention for sterilizing pathogens.

In step 901, pathogens are collected by an air filtration media with integrated disinfection capability. The air filtration media can be any of the filtration media described herein.

In step 903, the UV radiation source integrated with the filtration medium is activated on a predetermined schedule, typically under the direction of a control, such as controller 116.

In step 905, UV radiation is emitted into the filtration medium according to the predetermined schedule including at least one of a constant illumination mode, a duty cycle illumination mode, and an on-demand illumination mode (activated by a user).

It will be understood that one or more of the processes, sub-processes, and process steps described herein may be performed by hardware, firmware, software, or a combination of two or more of the foregoing, on one or more electronic or digitally-controlled devices for example adjusting the variable capacitors and/or the relative bobbin positions and/or the power level of the AC source 130. The software may reside in a software memory (not shown) in a suitable electronic processing component or system such as, for example, control 116. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), or application specific integrated circuits (ASICs). Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., control 116), direct the electronic system to carry out the instructions. The computer program product may be selectively embodied in any non-transitory computer-readable storage medium for use by or in connection with an instruction execution system, apparatus, or device, such as a electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical).

It will also be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

Statements of Invention

The following statements of the invention represent non-limiting aspects of the invention.

Statement 1. An air filtration media with integrated disinfection capability, comprising: a collection filter for capture of pathogens; and an ultraviolet (UV) radiation source integrated into the collection filter such that the pathogens collected by the collection filter are exposed to UV radiation from the UV radiation source.

Statement 2. The media of statement 1, further comprising: a housing holding the collection filter, and the UV radiation source is integrated into the collection filter via a light emitting diode disposed inside of a housing holding the collection filter.

Statement 3. The media of statement 2, wherein the light emitting diode is coupled to a radiation scattering and diffuser layer.

Statement 4. The media of statement 2, further comprising an optical fiber extending into the housing and configured to distribute the UV radiation along a length thereof.

Statement 5. The media of statement 4, wherein the optical fiber comprised Bragg gratings formed into outer surfaces of the optical fiber at different points along the length.

Statement 6. The media of statement 1, wherein the collection filter comprises a particle capture layer formed of nanofibers.

Statement 7. The media of statement 1, wherein the collection filter comprises a particle capture layer formed of patterned nanofibers.

Statement 8. The media of statement 1, wherein the collection filter comprises a high efficiency air filtration media having a figure of merit between 10 and 60 $kPa^{-1}$.

Statement 9. The media of statement 1, wherein the collection filter comprises in sequence: a particle capture layer which capture pathogens and an optically active layer which distributes radiation from the UV radiation source.

Statement 10. The media of statement 1, wherein the collection filter comprises in sequence: a first electromagnetic radiation scattering and diffuser layer, a particle capture layer which capture pathogens, an optically active layer which distributes radiation from the UV radiation source, and a second electromagnetic radiation scattering and diffuser layer.

Statement 11. The media of statement 1, wherein the collection filter comprises in sequence: a first shell layer, a first electromagnetic radiation scattering and diffuser layer, a particle capture layer which capture pathogens, an optically active layer which distributes radiation from the UV radiation source, a second electromagnetic radiation scattering and diffuser layer, and a second shell layer.

Statement 12. The media of statement 9 or statement 10 or statement 11, further comprising a wire mesh layer disposed against the particle capture layer.

Statement 13. The media of statement 9 or statement 10 or statement 11, wherein the ultraviolet radiation source comprises a light emitting diode which, when powered, emits the UV radiation into the optically active layer.

Statement 14. The media of statement 13, wherein the optically active layer distributes the UV radiation such that at least the particle capture layer is exposed to the UV radiation.

Statement 15. The media of statement 1, further comprising: a programmed controller configured to operate the UV radiation source on a predetermined schedule.

Statement 16. The media of statement 15, wherein the predetermined schedule programmed into the controller comprises at least one of a constant illumination mode, a duty cycle illumination mode, and an on-demand illumination mode.

Statement 17. The media of statement 1, wherein the collection filter comprises a nanofiber mat, wherein a thickness of the mat ranges from 0.10 vim to 10 mm.

Statement 18. The media of statement 1, wherein the collection filter comprises a nanofiber mat, wherein a thickness of the mat ranges from 2 to 5 microns.

Statement 19. The media of statement 1, wherein the collection filter comprises a nanofiber mat, wherein the mat comprises layers of nanofibers ranging from 4 to 4000 layers.

Statement 20. The media of statement 1, wherein the collection filter comprises a nanofiber mat, wherein the mat comprises layers of nanofibers ranging from 4 to 400 layers.

Statement 21. The media of statement 1, wherein the collection filter comprises a nanofiber mat, wherein the mat comprises layers of nanofibers ranging from 5 to 100 layers.

Statement 22. The media of statement 1, wherein the collection filter comprises a nanofiber mat, wherein the mat comprises layers of nanofibers ranging from 2 to 15 layers.

Statement 23. The media of statement 1, wherein the collection filter comprises a fiber mat having fibers of an average fiber diameter of less than 500 nm.

Statement 24. The media of statement 1, wherein the collection filter comprises a fiber mat having fibers of an average fiber diameter of less than 200 nm.

Statement 25. The media of statement 1, wherein the collection filter comprises a fiber mat having fibers of an average fiber diameter of less than 100 nm.

Statement 26 The media of statement 1, wherein the collection filter comprises a fiber mat having fibers of a diameter less 1 micron.

Statement 27. The media of statement 1, wherein the collection filter comprises a filtration medium having a figure of merit between 20 $kPa^{-1}$ and 40 $kPa^{-1}$.

Statement 28. The media of statement 1, wherein the collection filter comprises a filtration medium having a figure of merit between 40 $kPa^{-1}$ and 80 $kPa^{-1}$.

Statement 29. The media of statement 1, wherein the collection filter comprises a filtration medium having a figure of merit between 70 kPa and 80 $kPa^{-1}$.

Statement 30. A respirator comprising the media of any of statements 1-29.

Statement 31. A laminated face mask comprising the media of any of statements 1-29.

Statement 32. An air flow filter comprising the media of any of statements 1-29.

Statement 33. A HVAC unit comprising the media of any of statements 1-29.

Statement 34. A method for sterilizing pathogens utilizing the media of any of statements 1-29.

Statement 35. A garment comprising: in sequence, a first electromagnetic radiation scattering and diffuser layer, a particle capture layer which captures pathogens, an optically active layer which distributes ultraviolet radiation, and a second electromagnetic radiation scattering and diffuser layer.

Statement 36. The garment of statement 35, further comprising an ultraviolet radiation source coupling radiation into the optically active layer.

Statement 37. The garment of statement 36, wherein the ultraviolet radiation source in integrated into the garment.

Statement 38. The garment of statement 37, further comprising a fiber optic receiving ultraviolet radiation from the ultraviolet radiation source and dispersing the ultraviolet radiation along a length of the fiber optic.

Statement 39. A garment comprising: in sequence, a particle capture layer which captures pathogens, an optically active layer which distributes ultraviolet radiation.

Numerous modifications and variations of the invention are possible in light of the above teachings. It is therefore to be understood that within the scope of the appended claims, the invention may be practiced otherwise than as specifically described herein.

The invention claimed is:

1. An air filtration media with integrated disinfection capability, comprising:
a collection filter including a particle capture layer for capture of pathogens and comprising first and second electromagnetic radiation scattering and diffuser layers; and
an ultraviolet (UV) radiation source integrated into the collection filter and emitting UV radiation from in between the first and second electromagnetic radiation scattering and diffuser layers such that the pathogens collected by the collection filter are exposed to the UV radiation from the UV radiation source and disinfected within the collection filter by exposure to the UV radiation.

2. The media of claim 1, further comprising:

a housing holding the collection filter, and the UV radiation source is integrated into the collection filter via a light emitting diode disposed inside of a housing holding the collection filter.

3. The media of claim 2, wherein the light emitting diode is coupled to a radiation scattering and diffuser layer.

4. The media of claim 2, further comprising an optical fiber extending into the housing and configured to distribute the UV radiation along a length thereof.

5. The media of claim 4, wherein the optical fiber comprised Bragg gratings formed into outer surfaces of the optical fiber at different points along the length.

6. The media of claim 1, wherein the collection filter comprises a particle capture layer formed of nanofibers.

7. The media of claim 1, wherein the collection filter comprises a particle capture layer formed of patterned nanofibers.

8. The media of claim 1, wherein the collection filter comprises a high efficiency air filtration media having a figure of merit between 10 and 60 $kPa^{-1}$.

9. The media of claim 1, wherein the collection filter comprises in sequence:

a particle capture layer which capture pathogens and an optically active layer which distributes radiation from the UV radiation source.

10. The media of claim 9, further comprising a wire mesh layer disposed against the particle capture layer.

11. The media of claim 1, wherein the collection filter comprises in sequence:

a first electromagnetic radiation scattering and diffuser layer, a particle capture layer which capture pathogens, an optically active layer which distributes radiation from the UV radiation source, and a second electromagnetic radiation scattering and diffuser layer.

12. The media of claim 1, wherein the collection filter comprises in sequence:

a first shell layer, a first electromagnetic radiation scattering and diffuser layer, a particle capture layer which capture pathogens, an optically active layer which distributes radiation from the UV radiation source, a second electromagnetic radiation scattering and diffuser layer, and a second shell layer.

13. The media of claim 12, wherein the ultraviolet radiation source comprises a light emitting diode which, when powered, emits the UV radiation into the optically active layer.

14. The media of claim 13, wherein the optically active layer distributes the UV radiation such that at least the particle capture layer is exposed to the UV radiation.

15. The media of claim 1, further comprising:

a programmed controller configured to operate the UV radiation source on a predetermined schedule.

16. The media of claim 15, wherein the predetermined schedule programmed into the controller comprises at least one of a constant illumination mode, a duty cycle illumination mode, and an on-demand illumination mode.

17. A garment comprising:

in sequence, a first electromagnetic radiation scattering and diffuser layer, a particle capture layer which captures pathogens, an optically active layer which distributes ultraviolet radiation from inside the garment for pathogen disinfection within the garment by exposure to ultraviolet radiation, and a second electromagnetic radiation scattering and diffuser layer.

18. The garment of claim 17, further comprising an ultraviolet radiation source coupling radiation into the optically active layer.

19. The garment of claim 18, wherein the ultraviolet radiation source in integrated into the garment.

20. The garment of claim 17, further comprising a fiber optic receiving ultraviolet radiation from the ultraviolet radiation source and dispersing the ultraviolet radiation along a length of the fiber optic.

21. The media of claim 4, wherein the optical fiber distributes the UV radiation within the collection filter.

22. The media of claim 1, wherein the UV radiation emitted from in between the first and second electromagnetic radiation scattering and diffuser layers disinfects pathogens by direct exposure to the UV radiation.

23. The media of claim 22, where the UV radiation emitted from in between the first and second electromagnetic radiation scattering and diffuser layers does not activate a photocatalyst.

24. The media of claim 22, where the UV radiation emitted from in between the first and second electromagnetic radiation scattering and diffuser layers comprises germicidal UV radiation.

25. The media of claim 24, where the germicidal UV radiation comprises UV-C radiation.

* * * * *